(12) United States Patent
Lerebour et al.

(10) Patent No.: US 9,801,798 B2
(45) Date of Patent: Oct. 31, 2017

(54) MOISTURIZING COMPOSITION

(71) Applicant: L'OREAL, Paris (FR)

(72) Inventors: Geraldine Lerebour, Les Loges (FR); Catherine Marion, Antony (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/367,976

(22) PCT Filed: Dec. 21, 2012

(86) PCT No.: PCT/EP2012/076787
§ 371 (c)(1),
(2) Date: Nov. 24, 2014

(87) PCT Pub. No.: WO2013/093069
PCT Pub. Date: Jun. 27, 2013

(65) Prior Publication Data
US 2015/0080346 A1    Mar. 19, 2015

Related U.S. Application Data

(60) Provisional application No. 61/592,370, filed on Jan. 30, 2012.

(30) Foreign Application Priority Data

Dec. 23, 2011    (FR) ..................... 11 62423

(51) Int. Cl.
| | | |
|---|---|---|
| A01N 57/00 | (2006.01) |
| A61K 31/66 | (2006.01) |
| A61K 8/55 | (2006.01) |
| A61K 8/34 | (2006.01) |
| A61K 8/37 | (2006.01) |
| A61Q 19/08 | (2006.01) |
| A61Q 19/00 | (2006.01) |

(52) U.S. Cl.
CPC ............ *A61K 8/55* (2013.01); *A61K 8/345* (2013.01); *A61K 8/375* (2013.01); *A61Q 19/007* (2013.01); *A61Q 19/08* (2013.01); *A61K 2800/30* (2013.01)

(58) Field of Classification Search
None
See application file for complete search history.

(56) References Cited

U.S. PATENT DOCUMENTS

2007/0202062 A1*    8/2007    Workman et al. ............ 424/66

FOREIGN PATENT DOCUMENTS

| DE | 102006046076 A1 | 4/2007 |
| EP | 2243462 A1 | 10/2010 |
| FR | 2795956 A1 | 1/2001 |
| WO | WO-2007/103555 A2 | 9/2007 |

OTHER PUBLICATIONS

Mendoza, "Effect of genetically modified low phytic acid plants on mineral absorption," International Journal of Food Science and Technology 2002, 37, 759-767 (Abstract).*

* cited by examiner

*Primary Examiner* — Jared D Barsky
(74) *Attorney, Agent, or Firm* — Polsinelli PC

(57) ABSTRACT

The present invention relates to a composition, in particular a cosmetic composition, comprising, in a physiologically acceptable medium, at least glyceryl caprylate, 1,3-propanediol and phytic acid or any of the salts thereof, said composition being free from perlite.

The present invention further relates to a composition, in particular a cosmetic composition, comprising, in a physiologically acceptable medium, at least glyceryl caprylate, 1,3-propanediol and phytic acid or any of the salts thereof.

9 Claims, No Drawings

MOISTURIZING COMPOSITION

CROSS REFERENCE TO RELATED APPLICATIONS

This application is a National Phase filing under 35 U.S.C. §371 of PCT/EP2012/076787 filed on Dec 21, 2012, and this application claims priority to Application No. 1162423 filed in France on Dec. 23, 2012. PCT/EP2012/076787 also claims the benefit of U.S. Provisional Application No. 61/592,370 filed on Jan. 30, 2012. The entire contents of each application are hereby incorporated by reference.

The present invention relates to the field of cosmetics, and skin moisturization in particular. The present invention particularly relates to a cosmetic care method for attenuating dehydration lines, particularly on the face or around the eyes.

Dehydration lines may appear on the skin, in cases of dry skin, particularly with skin ageing. These lines are considered to be unsightly particularly in the more visible areas of the human body such as the hands or face, particularly in the periocular region.

The contour of the eye is a particularly fragile and complex area due to the structure thereof. This area is much thinner than the rest of the face. The area is subject to considerable use since the eyelid is in motion to ensure that the cornea is continuously hydrated. The skin tissue of the eye contour is very elastic and looser than most of the other parts of the body and face, making this area particularly fragile and subject to the appearance of dehydration lines or wrinkles.

To combat the natural appearance of dehydration lines or wrinkles, applying cosmetic compositions promoting moisturization of the application areas onto the skin is known. Improving skin moisturization is thus a component of an anti-wrinkle treatment.

Numerous cosmetic compositions for improving skin moisturization are known. However, there is a need for novel compositions having a satisfactory moisturizing efficacy while having satisfactory sensory properties, such as a silky texture. Unfortunately, cosmetic moisturizing compositions may further give rise to an unsightly "corrugated sheet" effect, despite the moisturizing effect, characterized by folds on the skin surface, a somewhat wrinkled effect, with the skin retracting and creating false wrinkles.

Thus the aim of the present invention is that of providing a composition, in particular a cosmetic composition, in particular a moisturizing composition, particularly for attenuating skin dehydration lines, and preferably having a non-existent or lessened "corrugated sheet" effect.

The aim of the present invention is also that of providing a composition, in particular a cosmetic composition having a satisfactory texture, which is preferably pleasant, silky, particularly for the application thereof onto the skin. In particular, the aim of the present invention is that of providing a composition, in particular a cosmetic composition having a suitable texture, spreading behavior, penetration rate and skin texture.

It has surprisingly been discovered that a composition, in particular a cosmetic composition, comprising at least three particular chemical compounds made it possible to achieve the aims mentioned above.

The invention relates more specifically to a composition, in particular a cosmetic composition, comprising, in a physiologically acceptable medium, at least glyceryl caprylate, 1,3-propanediol and phytic acid or any of the salts thereof.

The inventors discovered that a composition, in particular a cosmetic composition, comprising this association or combination of glycerol caprylate (also referred to as glyceryl caprylate), 1,3-propanediol and phytic acid or any of the salts thereof makes it possible to attenuate dehydration lines. This composition, when applied to the skin, gives rise to a non-existent or lessened "corrugated sheet" effect compared to a composition not comprising this association or combination.

Moreover, the composition according to the invention has a pleasant texture, particularly when applied to the skin. The composition according to the invention has a satisfactory texture, spreading behavior, penetration rate and skin texture. In particular, the composition according to the invention leaves a very light oily and silky residual film, which is sought.

Glyceryl caprylate is a monoester of glycerin and caprylic acid. By way of example, mention may be made of the product sold under the trade name dermosoft® GMCY by DR STRAETMANS GmbH.

1-3-propanediol may be advantageously obtained from DUPONT TATE AND LYLE BIO PRODUCTS under the trade name Zemea® Propanediol.

Preferably, the phytic acid salt is an alkaline phytic acid salt, and more preferably is sodium phytate. Sodium phytate may be advantageously obtained from DR STRAETMANS GmbH under the trade name dermofeel® PA-3.

Advantageously, the composition according to the invention comprises not more than 1.5% by weight of glyceryl caprylate, with respect to the total weight of the composition.

Advantageously, the composition according to the invention comprises not more than 25% by weight of 1,3-propanediol, with respect to the total weight of the composition.

Advantageously, the composition according to the invention comprises not more than 0.3% by weight of phytic acid or any of the salts thereof, with respect to the total weight of the composition.

Advantageously, the composition according to the invention comprises:
  not more than 1.5% by weight of glyceryl caprylate, with respect to the total weight of the composition; and
  not more than 25% by weight of 1,3-propanediol, with respect to the total weight of the composition; and
  not more than 0.3% by weight of phytic acid or any of the salts thereof, and particularly sodium phytate, with respect to the total weight of the composition.

In particular, the present invention comprises not more than 1.5%, preferably 0.01% to 5% by weight, and more preferably 0.1% to 1.5% by weight of glyceryl caprylate with respect to the total weight of the composition.

In particular, the present invention comprises not more than 25%, preferably 0.1% to 25% by weight, and more preferably 0.5 to 10% by weight of 1,3-propanediol with respect to the total weight of the composition.

In particular, the present invention comprises not more than 0.3%, preferably 0.01% to 1.5% by weight, and more preferably 0.05% to 0.3% by weight of phytic acid or any of the salts thereof with respect to the total weight of the composition.

According to one particular alternative embodiment, the composition according to the invention further comprises an alcohol, in particular a $C_2$-$C_8$ alcohol, other than 1,3-propanediol, and preferably comprises ethyl alcohol. Preferably, the composition comprises 0.1 to 25%, and preferably 0.1 to 10%, and more preferably 0.1% to 5%, by weight of alcohol other than 1,3-propanediol, and preferably of ethyl alcohol, with respect to the total weight of the composition.

According to one alternative embodiment, the composition according to the invention is free from perlite.

Perlite is a natural glass of volcanic origin, glossy light gray or black in color, resulting from the rapid cooling of lava and presented in the form of small particles resembling pearl. Perlite particles are particularly commercially available from WORLD MINERALS EUROPE under the trade name Perlite P1430, Perlite P2550 or Perlite P2040. Perlite is excluded according to this alternative embodiment since it may be used in compositions contrary to the aim of the invention and the objective of skin moisturization.

The composition according to the present invention is preferably a cosmetic or dermatological composition, and more preferentially a cosmetic composition.

The term "physiologically acceptable medium" is intended to denote a medium compatible with human keratin materials and/or fibers, such as for example, non-exhaustively, the skin, mucosa, nails, scalp and/or hair.

This physiologically acceptable medium generally comprises water, optionally mixed with one or a plurality of organic solvents.

The composition according to the invention may also comprise an oily phase, which may comprise oils, gums, waxes routinely used in the field of application in question.

Preferably, the composition further comprises one or a plurality of fats, like cetylstearyl alcohol, dicaprylyl carbonate, sunflower oil, shea butter, a mixture of plant origin of lecithin, fatty acids and fatty alcohol, one or a plurality of polymers such as a scleroglucan gum, xanthan, one or a plurality of polysaccharides, such as glucose, mannose and/or glucuronic acid, one or a plurality of solvents such as glycerol, water, one or a plurality of surfactants such as a citric ester of glycerol stearate, and/or a plurality of vitamins such as tocopherol (alpha, beta, gamma and/or delta), and/or one or a plurality of preservatives, such as benzyl acid. Preferably, the composition according to the invention comprises 5 to 35% by weight of fats, 0 to 5% by weight of polymer(s), 65 to 95% of solvent(s), and 0 to 5% of surfactant(s). The term "0%" covers alternative embodiments where the compound is absent, and where it is present in detectable traces.

The cosmetic compositions according to the invention may contain routine cosmetic additives: pigments, colorants, biological active constituents (anti-age, anti-oily skin, brightening, whitening, anti-oxidants, etc.), sun filters, film-forming polymers, oils, fats, hydrating agents, emollients, solvents, surfactants, vitamins, and/or preservatives, or other cosmetic excipients.

The compositions according to the invention may be in any galenic form suitable for the use according to the present invention, and in particular in the form of gel, serum, direct, inverse or multiple emulsions, sticks, hot-poured products, loose or compact powders, or creams.

Advantageously, the composition according to the invention is in the form of an emulsion, particularly in the form of an Oil-in-Water (O/W) emulsion.

According to one alternative embodiment, the composition, which is preferably free from perlite, is not a deodorant.

The invention also relates to a method for preparing a cosmetic composition according to the invention, the method comprising the mixture of glyceryl caprylate, 1,3-propanediol and phytic acid or any of the salts thereof, in particular sodium phytate, with cosmetic excipients, and optionally with one or a plurality of cosmetic active ingredients.

The invention also relates to the use of a composition, in particular a cosmetic composition, according to the invention for moisturizing skin. In particular, the composition according to the invention is applied to at least one area of the skin having dehydration lines, such as the hands or face, in particular the forehead, cheeks, or contour of an eye (periocular region), and in particular crow's feet, the area below the eye (bag), eyelids, neck, feet, legs, arms, forearms, or any other dry area of the body.

In particular, the invention relates to the use of a composition, in particular a cosmetic composition, comprising, in a physiologically acceptable medium, at least glyceryl caprylate, 1,3-propanediol and phytic acid or any of the salts thereof, and in particular sodium phytate, for moisturizing skin.

The invention further relates to a cosmetic care method comprising the application onto the skin of a composition, in particular a cosmetic composition, according to the invention, comprising in a physiologically acceptable medium, at least glyceryl caprylate, 1,3-propanediol and phytic acid or any of the salts thereof, and in particular sodium phytate. Typically, the method according to the invention comprises the application of a composition according to the invention to a skin area in need thereof.

All the alternative embodiments, embodiments, preferences, or particular aspects of the compositions according to the invention apply to the uses and methods as defined in the invention.

According to one particular alternative embodiment, the composition is free from perlite.

Advantageously, the method reduces visible skin wrinkles and fine lines, particularly on the face, and especially around the eyes and on the eyelids.

Advantageously, the composition according to the invention is applied to dry and/or aged skin According to one preferred alternative embodiment, these methods comprise the application of the composition to an area chosen from the hands, face, in particular the forehead, cheeks, or contour of an eye (periocular region), and in particular crow's feet, the area below the eye (bag), eyelids, neck, feet, legs, arms, forearms, or any other dry area of the body.

Preferably, said skin area has dehydration lines.

Preferably, the composition according to the invention is applied to an area other than the armpits.

The present invention particularly relates to a care method for dry skin.

We will now give concrete examples illustrating the invention, but that are in no way limitative.

All percentages given in the examples are given by weight, unless specified otherwise, and the temperature is expressed in degrees Celsius unless specified otherwise, and the pressure is atmospheric pressure, unless specified otherwise. In the examples, the amounts of the ingredients of the compositions are given as a % by weight with respect to the total weight of the composition.

EXAMPLES

Example 1

Cosmetic Composition Formulations

Two cosmetic compositions were prepared so as to be comparable in respect of the addition effect in the glycerol caprylate, sodium phytate and 1,3-propanediol composition.

The compositions under test are as follows:

TABLE 1

| EU INCI | Comparative composition 1C (% by weight) | Composition 1 according to the invention (% by weight) |
|---|---|---|
| BENZYL ALCOHOL | 0.5 | 0.5 |
| CETEARYL ALCOHOL | 0.5 | 0.5 |
| DICAPRYLYL CARBONATE | 3 | 3 |
| C12-16 ALCOHOLS (and) PALMITIC ACID (and) HYDROGENATED LECITHIN (BIOPHILIC H from LUCAS MEYER COSMETICS) | 4 | 4 |
| *HELIANTHUS ANNUUS* SEED OIL | 3 | 3 |
| *BUTYROSPERMUM PARKII* BUTTER | 5 | 5 |
| SODIUM PHYTATE (dermofeel ® PA-3 from DR STRAETMANS GmbH) | — | 0.1 |
| SCLEROTIUM GUM | 0.3 | 0.3 |
| XANTHAN GUM | 0.1 | 0.1 |
| GLYCERIN | 5 | 5 |
| PROPANEDIOL (Zemea ® Propanediol from DUPONT TATE AND LYLE BIO PRODUCTS) | — | 3 |
| ETHYLIC ALCOHOL. | — | 3 |
| AQUA | qs 100 | qs 100 |
| GLYCERYL CAPRYLATE (dermosoft ® GMCY from DR STRAETMANS GmbH) | — | 0.5 |
| GLYCERYL STEARATE CITRATE | 1 | 1 |
| TOCOPHEROL | 0.025 | 0.025 | qs 100: Sufficient quantity to make up to 100% of the total weight of the composition The following examples summarize the results obtained by applying these compositions (comparative or according to the invention) to the facial skin, particularly around the eye contour, of a panel of six women:

0.30 ml of each formula was applied for each half-face, in a randomized fashion. The evaluation was performed immediately (2 minutes) after application versus bare skin, by expert beauticians.

According to the Protocol

The panel firstly evaluated the comparative composition versus bare skin, and secondly the composition according to the invention versus bare skin. As mentioned above, each application is performed on one half of the face, the other half of the face thus representing bare skin.

In the interval between 2 applications, the panel removed the treatment completely and cleansed their face.

The effects are rated on a 7-point scale that may be positive and/or negative, with a reference "parameter under evaluation not applicable for volunteer".

The summarized data are compiled in tables 2 to 5.

TABLE 2

Effect on dehydration lines

| Parameters under evaluation | | Formulas | Cases concerned/ Total cases | Accentuates visibility | | | | | | | | Attenuates visibility | | | | | Overall Score | |
|---|---|---|---|---|---|---|---|---|---|---|---|---|---|---|---|---|---|---|
| | | | | −6 | −5 | −4 | −3 | −2 | −1 | 0 | 1 | 2 | 3 | 4 | 5 | 6 | − | + |
| Dehydration lines | Eyes | Composition 1 according to the invention | 6/6 | | | | | | | | | 1 | 4 | 1 | | | | 18 |
| | | Comparative composition 1C | | | | | | | −1 | | 1 | 2 | 3 | | | | | | 8 |
| | Face | Composition 1 according to the invention | 6/6 | | | | | | | | | | 3 | 3 | | | | 21 |
| | | Comparative composition 1C | | | | | | | | | 2 | 2 | 2 | | | | | | 12 |

It was observed that the composition according to the invention is more effective (markedly superior) in respect of attenuating dehydration lines, particularly on the face and around the eyes, than the comparative composition.

TABLE 3

Effect on wrinkles

| Parameters under evaluation | | Formulas | cases concerned/ total cases | ACCENTUATES visibility | | | | | | | ATTENUATES visibility | | | | | | OVERALL SCORE | |
|---|---|---|---|---|---|---|---|---|---|---|---|---|---|---|---|---|---|---|
| | | | | -6 | -5 | -4 | -3 | -2 | -1 | 0 | 1 | 2 | 3 | 4 | 5 | 6 | − | + |
| Wrinkles | Lower eyelid | Composition 1 according to the invention | 6/6 | | | | | | | | | 2 | 3 | 1 | | | | 18 |
| | | Comparative composition 1C | | | | | | | | 4 | | 2 | | | | | | 4 |
| | Cheeks | Composition 1 according to the invention | 4/6 | | | | | | | | | 3 | 1 | | | | | [9] |
| | | Comparative composition 1C | | | | | | | 1 | 3 | | | | | | | [−1] | |
| | Forehead | Composition 1 according to the invention | 6/6 | | | | | | | 5 | 1 | | | | | | | 2 |
| | | Comparative composition 1C | | | | | | | | 6 | | | | | | | 0 | 0 |

The composition according to the invention displays a markedly superior efficacy for attenuating wrinkles than the comparative composition on the lower eyelids, cheeks and forehead.

TABLE 4

Effect on bags

| Parameters under evaluation | | Formulas | cases concerned/ total cases | ACCENTUATES visibility | | | | | | | ATTENUATES visibility | | | | | | Overall score | |
|---|---|---|---|---|---|---|---|---|---|---|---|---|---|---|---|---|---|---|
| | | | | -6 | -5 | -4 | -3 | -2 | -1 | 0 | 1 | 2 | 3 | 4 | 5 | 6 | − | + |
| Unevenness in skin surface | Bags | Composition 1 according to the invention | 6/6 | | | | | | | 1 | 2 | 2 | 1 | | | | −1 | 5 |
| | | Comparative composition 1C | | | | | | | | 1 | 5 | | | | | | −1 | |

The composition according to the invention makes it possible to attenuate unevenness in the skin surface, particularly bags, better than the comparative composition. This action may be explained by the action of the composition on wrinkles. The effects observed with Composition 1 C are practically non-existent.

TABLE 5

"Corrugated sheet" effect

| | Grading of effects | | | | | | | |
|---|---|---|---|---|---|---|---|---|
| "Corrugated sheet" result | NONE 0 | Very slight 1 | Slight 2 | Moderate 3 | Relatively significant 4 | Significant 5 | Very significant 6 | Overall Score |
| Composition 1 according to the invention | 6 | | | | | | | 0 |
| Comparative composition 1C | 2 | | 2 | 1 | | 1 | | 12 |

The composition according to the invention thus exhibits a significant efficacy on dehydration lines with no "corrugated sheet" effect, unlike a comparative composition without the association according to the invention (glycerol caprylate, sodium phytate and 1,3-propanediol).

Evaluation of Appearances of Formulations and Cosmetic Applications

The comparative composition and the composition according to the invention have textures of gelled creams of relatively high densities.

The comparative composition does not spread as well as the composition according to the invention.

The composition according to the invention spreads in a slightly oily, silky and waxy film both on the face and between the fingers. The spreading thereof is thus completely satisfactory and pleasant.

Unlike the comparative composition, the composition according to the invention has a superior skin texture after application. The composition according to the invention leaves a very light oily and silky residual film.

The invention claimed is:

1. A cosmetic composition, comprising, in a physiologically acceptable medium, 0.01% to 5% by weight of glyceryl caprylate with respect to the total weight of the composition, 0.5% and to 10% by weight of 1,3-propanediol with respect to the total weight of the composition and 0.01% to 1.5% by weight of phytic acid or any of the salts thereof with respect to the total weight of the composition, said composition being free from perlite.

2. The composition according to claim 1, wherein the phytic acid salt is an alkaline phytic acid salt.

3. The composition according to claim 2, wherein the alkaline phytic acid salt is sodium phytate.

4. The composition according to claim 1, wherein it further comprises an alcohol other than 1,3-propanediol.

5. The composition according to claim 1, which further comprises 0.1% to 25% by weight of alcohol other than 1,3-propanediol with respect to the total weight of the composition.

6. The composition according to claim 2, wherein it comprises 0.01% to 5% by weight of glyceryl caprylate with respect to the total weight of the composition.

7. The composition according to claim 3, wherein it comprises 0.01% to 5% by weight of glyceryl caprylate with respect to the total weight of the composition.

8. The composition according to claim 1, which comprises 0.1% to 1.5% by weight of glyceryl caprylate; 0.5% to 10% by weight of 1,3 propanediol with respect to the total weight of the composition, and 0.05% to 0.3% by weight of phytic acid or any of the salts thereof with respect to the total weight of the composition.

9. The composition according to claim 1, which further comprises 0.1% to 10% by weight of a C2-C8 alcohol other than 1,3-propanediol with respect to the total weight of the composition.

* * * * *